(12) United States Patent
Courtot

(10) Patent No.: US 10,010,570 B2
(45) Date of Patent: *Jul. 3, 2018

(54) GALENICAL SOLID

(71) Applicant: LOëN HOLDING S.A.R.L., Luxembourg (LU)

(72) Inventor: Lionel Roland Courtot, Perouges (FR)

(73) Assignee: LOëN HOLDING S.A.R.L., Luxembourg (LU)

(*) Notice: Subject to any disclaimer, the term of this patent is extended or adjusted under 35 U.S.C. 154(b) by 150 days.

This patent is subject to a terminal disclaimer.

(21) Appl. No.: 14/983,691

(22) Filed: Dec. 30, 2015

(65) Prior Publication Data

US 2017/0128510 A1    May 11, 2017

(30) Foreign Application Priority Data

Nov. 5, 2015  (BE) .................................. 2015/5720

(51) Int. Cl.
| | | |
|---|---|---|
| *A61K 36/00* | (2006.01) | |
| *A61K 36/288* | (2006.01) | |
| *A61K 9/00* | (2006.01) | |
| *A61K 36/185* | (2006.01) | |
| *A61K 36/28* | (2006.01) | |
| *B65D 75/36* | (2006.01) | |
| *A23L 29/25* | (2016.01) | |
| *A23L 29/256* | (2016.01) | |
| *A23L 33/105* | (2016.01) | |

(52) U.S. Cl.
CPC ............ *A61K 36/288* (2013.01); *A23L 29/25* (2016.08); *A23L 29/256* (2016.08); *A23L 33/105* (2016.08); *A61K 9/0053* (2013.01); *A61K 36/185* (2013.01); *A61K 36/28* (2013.01); *B65D 75/36* (2013.01)

(58) Field of Classification Search
CPC ...................................................... A61K 36/00
See application file for complete search history.

(56) References Cited

U.S. PATENT DOCUMENTS

2013/0216596 A1* 8/2013 Viladot Petit ............ A61K 8/11
424/401

* cited by examiner

*Primary Examiner* — Qiuwen Mi
(74) *Attorney, Agent, or Firm* — Dinsmore & Shohl LLP

(57) ABSTRACT

Preparation process for dietary supplements, comprising at least two steps, the first step of which is to obtain a basic composition comprising liquid vegetable extracts (that contain alcohol), essential oils, water and optionally powdered vegetable extracts, mineral elements, vitamins, vegetable oils, marine plasma, organic silica, etc., and the second step of which is used to solidify the mixture by adding a solidifying premix comprising alginates, a vegetable gum and optionally solidification retarders such as dry hydrophilic plants, water chelators or other substances, even chemicals. The advantage of the process is that it enables dietary supplements to be obtained in a dry solid state that can be stored at ambient temperature or in a refrigerator, and is stable over time, without losing the nutritional and therapeutic value of the vegetable or natural substances contained therein.

3 Claims, 2 Drawing Sheets

GALENICAL SOLID

CROSS-REFERENCE TO RELATED APPLICATIONS

This application claims priority of Belgian Patent Application No. 2015/5720 filed Nov. 5, 2015.

FIELD OF THE INVENTION

The invention concerns dietary supplements in a solid form, comprising natural active substances with a therapeutic and/or nutritional effect, and gastro-resistants, intended for human or animal consumption.

More specifically, the purpose of the invention is to provide dietary supplements containing plant extracts, essential oils and other natural ingredients.

BACKGROUND OF THE INVENTION

These materials have a flavour that is too bitter, repugnant, too acidic, too metallic or cumbersome to enable consumption of these materials in their native or natural state.

Examples of these materials are chemotyped essential oils, fresh medicinal plant extracts in liquid form, dry medicinal plant extracts (bark, roots) in powdered form, vitamins, minerals, vegetable oils, etc.

Often these materials are administered in liquid form. Such a galenic liquid is completely suited by its nature, its odour and flavour to the dietary habits of herbivores, but it becomes a real barrier for the treatment of omnivores and carnivores who are completely repulsed by the olfactory and flavour characteristics of these products, and who can also suffer from problems in their digestive system.

In order to avoid the disadvantages of a galenic liquid, it is necessary to convert dietary supplements into a more solid state such as controlled solidification or gelification.

In order to maintain the full preservation of the active substances it is necessary to work with the same formulations and raw materials, and this in a cold process.

SUMMARY OF THE INVENTION

In searching for a usable process, an analysis of the components of the formulations of natural products has been conducted to identify the components that foster or inhibit gelification.

It results from this that the component that fosters gelification is water, and that the components able to inhibit gelification are alcohol and essential oils, which rather foster precipitation or a separation of phases, which by definition separate the different components.

The following products are known gelling agents:
pork gelatin;
gum arabics;
agar;
alginates.

Pork gelatin is ruled out as it is of a non-vegetable origin.

Gum arabics thicken the target products, but they systematically remain in a paste form without ever solidifying.

Agar, although effective, presents the drawback of involving a hot process, reaching a temperature of 90° C., which largely eliminates the alcohol and essential oils and consequently also a large proportion of the natural active substances.

In order to obtain an end product with the same consistency as a conventional gelatinous sweet, but without losing the activity of its components of a natural origin, the following has proven to be effective in our experiments.

Step I: Basic Composition

In a first step a basic composition is obtained, consisting of:
1—Plant extracts in liquid form concentrated in active constituents (phytotherapy):
    between 20 and 70%;
2—Essential oils (aromatherapy):
    between 1 and 15%;
3—Water:
    between 20 and 60%;
Optional:
4—Plant extracts in powdered form concentrated in active constituents (phytotherapy);
5—Minerals (oligotherapy);
6—Vitamins;
7—Vegetable oils;
8—Marine plasma;
9—Organic silicon (anticaking agent).

For the plant extract, medicinal plants can be used in the form of:
hydroalcoholic extracts, obtained by extraction;
hydroalcoholic glycerine extracts, obtained by extraction;
mother tinctures, obtained by extraction;
glycerine macerated buds, obtained by extraction;

For the plant extract used for phytotherapy, it can be derived from all possible plants, such as:
*Alchemilla vulgaris* HAG, with the part used being the above-ground bloom (origin: France);
*Ginkgo biloba* HA;
*Melilotus* TM;
*Cichorium intybus*, with the part used in powdered form being the root (origin: France);

The essential oils are obtained by distilling aromatic plants.

For aromatherapy, all essential oils can be used, such as for example:
*Citrus limomum*, with the part used being expressed zest (origin: Italy);
*Ocimum Basilicum*, with the part used being the flowering plant (origin: Vietnam);
*Mentha piperita*, with the part used being the flowering plant (origin: India).

The vegetable oils can be all possible oils, such as:
*Ricinus communis;*
*Vitis vinifera;*
*Corylus avellana.*

The mineral elements can be all possible minerals, such as:
zinc (Zn)
silicon (Si)
magnesium (Mg).

Step II: Solidifying premix and providing gastro-resistance.

In a second step a solidifying premix is added, consisting of:
Alginates (e.g.: brown algae E401) and Calcium (calcium sulphate) with a gelling effect and providing the gastro-resistance of the product.
Vegetable gum(s) with an emulsifying, binding and thickening effect (examples: Karaya gum, Sterculia, Gum arabic or Acacia senegal gum extract, etc):

Optional:
Natural or chemical substances with a retarding effect (examples: water chelators such as *Bambusa bamboo*, calcium chelators such as polyphosphates, monosaccharides, etc);
Dry hydrophilic plant (e.g: *Plantago ovata*);
Natural or chemical substances with an anti-foaming and anticaking effect (e.g.: silicon dioxide E551);
Natural or chemical flavourings (example: vanilla);
Natural or chemical food colourings (e.g.: beetroot);
Other substances, even chemicals, also providing the gastro-resistance of the active substances.

This process has resulted in dietary supplements in a solid form that remain dry while the nutritional and therapeutic value of the vegetable substances (natural active substances) is preserved thanks to the solidifying premix added at ambient temperature.

An advantage of the process described is that it enables gastro-resistant dietary supplements for human or animal consumption to be provided, that are no longer distasteful for the consumer because of their olfactory and flavour characteristics and which are no longer troublesome for his digestive system.

Another advantage of the process described is that it enables dietary supplements to be kept in a dry and solid form without refrigeration, which facilitates the transport and storage of these products.

BRIEF DESCRIPTION OF THE DRAWINGS

For greater clarity, a few example embodiments of dietary supplements are given, with reference to the accompanying drawings, wherein.

DETAILED DESCRIPTION OF THE PREFERRED EMBODIMENTS

Figure 1:
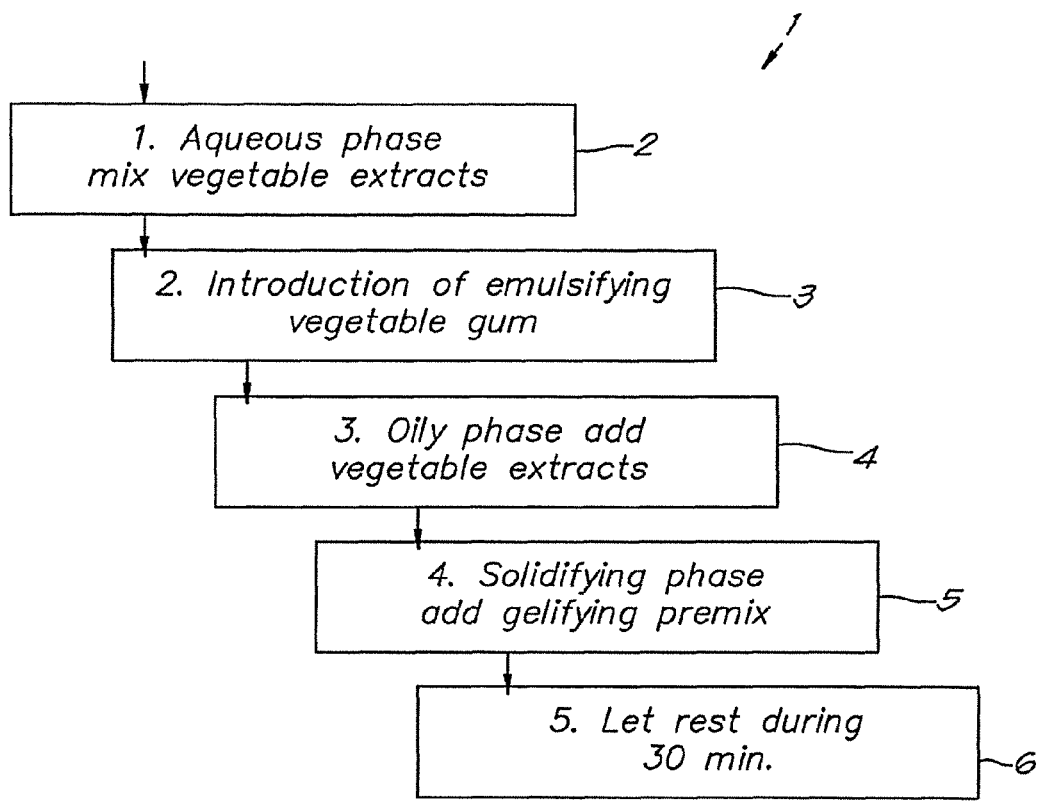
FIG. 1 schematically shows the steps of the production process according to the invention.

FIG. 1 shows the successive phases of the production process for dietary supplements 1 according to the invention, consisting of:
1. The aqueous phase 2 in which the vegetable extracts are mixed;
2. The introduction of an emulsifying vegetable gum 3;
3. The oil phase 4 introducing the vegetable extracts in the form of oils;
4. The solidification phase 5 with the introduction of the gelling premix, in order to emulsify until a paste is obtained;
5. The rest phase 6 allowing the solidifying premix to act until a stable solid is obtained.

Figure 2:
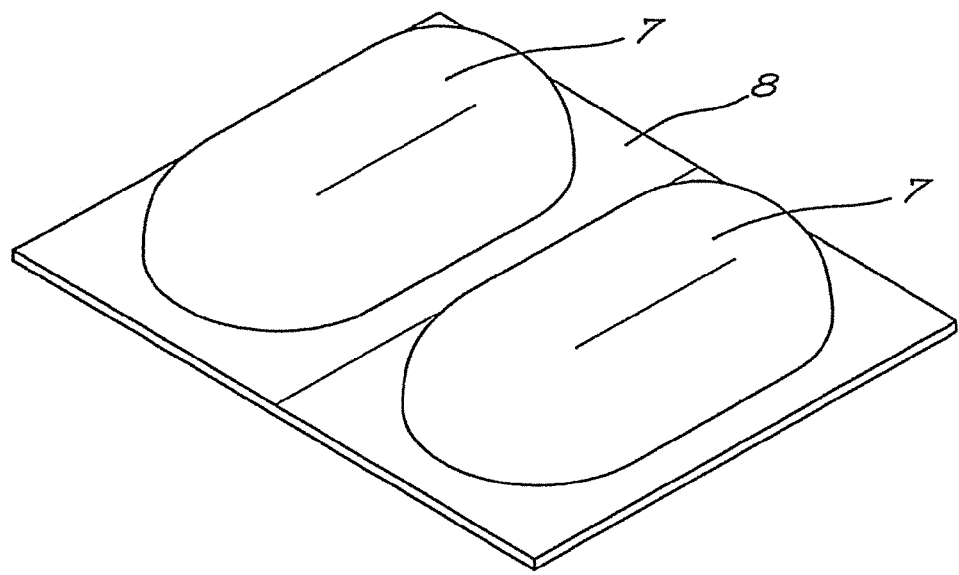
FIG. 2 is a perspective view of a dietary supplement formed by the process of the invention.

FIG. 2 shows a dietary supplement formed by the process of the invention, in the form of an individual capsule 7 in a blister pack 8, although loose capsules can also be supplied in a jar, for example.

Figure 3:
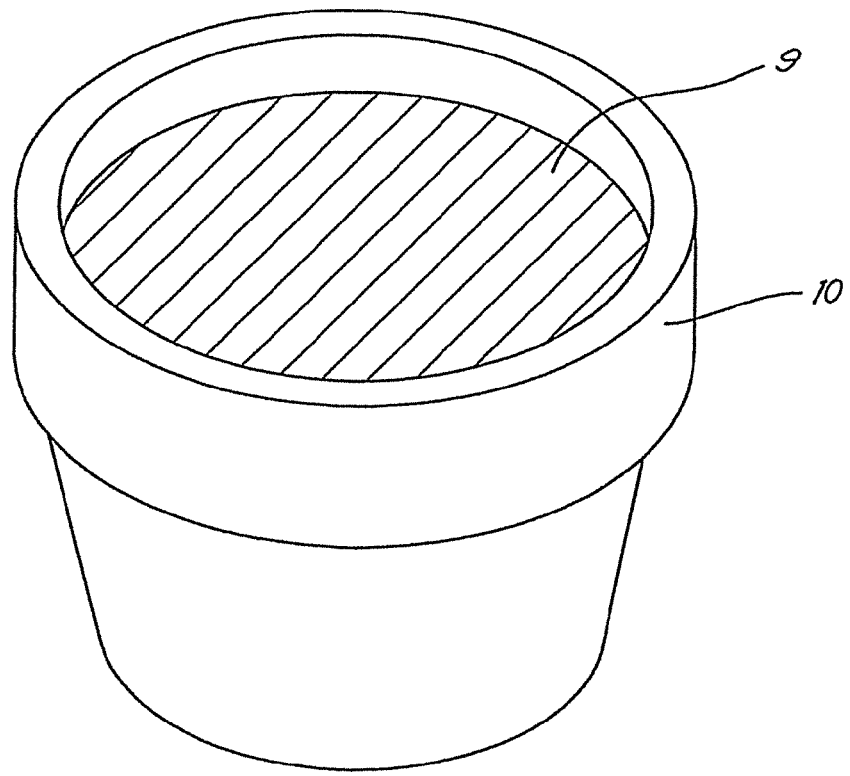
FIG. 3 is a perspective view of another dietary supplement formed by the process of the invention.

FIG. 3 shows another example of a dietary supplement formed by the process of the invention in the form of a paste 9 in a pot 10.

It is clear that the dietary supplement can come in any form, such as a syringe, sweets, etc.

It follows from this that a dietary supplement, obtained by the process described, can be used for the preventive or therapeutic treatment of people or animals by oral administration, as the production process is able to preserve the natural substances of the plants without losing their nutritional and therapeutic value, while being limited to ambient temperatures.

In order to illustrate the production process according to the invention, the application of the production process to a dietary supplement, i.e. a product aimed at "drainage" in particular, is described as an example hereinafter:
1) Mixing in the aqueous phase:
Water: 35%
Marine plasma: 10%
Colloidal silicon: 5%
Extract* of above-ground parts of stinging nettle (*urtica doioica*): 10%
Extract* of dandelion root (*Taraxacum officinalis*): 15%
Extract* of artichoke leaves and roots (*Cynara scolymus*): 10%
*: hydroalcoholic glycerine extracts or hydroalcoholic extracts.
2) Introduction of the gum arabic and emulsification:
Gum arabic: 1%
3) Continuation of the emulsification of the aqueous phase, while introducing the oil phase:
Eucalyptus essential oil (*Eucalyptus globulus*): 2%
Bitter orange essential oil (*Citrus aurantium*): 1%
Cypress essential oil (*Cupressus sempervirens*): 1%
4) In the solidification phase, introduction of the gelling premix and the powdered plants prepared beforehand, then mixing.
Chlorella powder (*Chlorella pyrenoidosa*): 2%
Sodium alginate: 7.8%
Calcium sulphate: 0.1%
Xanthan gum: 0.1%
5) Leave to rest until solidification (approximately 30 minutes).

It is clear that the invention is by no means limited to the examples described above, but that many modifications can be made to the form and composition of the dietary supplements while respecting the production process described above without departing from the scope of the invention as defined in the following claims.

The invention claimed is:
1. A preparation process for dietary supplements comprising the following steps:
in a first step a basic composition is obtained, consisting of:
1—Plant extracts in liquid form concentrated in active constituents between 20 and 70%;
2—Essential oils between 1 and 15%; and
3—Water between 20 and 60%;
in a second step a solidifying premix is added, consisting of:
Alginates and calcium sulphate with a gelling effect; and
Vegetable gum(s) with an emulsifying, binding and thickening effect.
2. A preparation process for dietary supplements comprising the following steps:
in a first step a basic composition is obtained, consisting of:
1—Plant extracts in powdered form concentrated in active constituents;
2—Minerals;
3—Vitamins;
4—Vegetable oils;
5—Marine plasma; and
6—Organic silicon;

in a second step a solidifying premix is added, consisting of:
  Alginates and calcium sulphate with a gelling effect; and
  Vegetable gum(s) with an emulsifying, binding and thickening effect.

3. A preparation process for dietary supplements comprising the following steps:
in a first step a basic composition is obtained, consisting of:
  1—Plant extracts in powdered form concentrated in active constituents;
  2—Minerals;
  3—Vitamins;
  4—Vegetable oils;
  5—Marine plasma; and
  6—Organic silicon;
in a second step a solidifying premix is added, consisting of:
  Natural or chemical substances with a retarding effect;
  Dry hydrophilic plant; and
  Other substances, even chemicals, also providing the gastro-resistance of the active substances.

\* \* \* \* \*